United States Patent [19]

Vöpel et al.

[11] 4,075,292
[45] Feb. 21, 1978

[54] PRODUCTION OF O,O-DIALKYL-PHOSPHOROCHLORIDOTHIONATES

[75] Inventors: Karl Heinz Vöpel, Kansas City, Mo.; Friedrich Hellrung, Nievenheim-Ueckerath; Otto Berendes, Dormagen, both of Germany

[73] Assignee: Bayer Aktiengesellschaft, Leverkusen, Germany

[21] Appl. No.: 691,957

[22] Filed: June 1, 1976

[51] Int. Cl.$^2$ .............................................. C07F 9/146
[52] U.S. Cl. ................................................... 260/986
[58] Field of Search ........................................ 260/986

[56] References Cited

U.S. PATENT DOCUMENTS

| 3,836,610 | 9/1974 | Diveley | 260/986 |
| 3,897,523 | 7/1975 | Sorstokke | 260/986 |

Primary Examiner—Anton H. Sutto
Attorney, Agent, or Firm—Burgess, Dinklage & Sprung

[57] ABSTRACT

An O,O-dialkyl-dithiophosphoric acid ester is reacted in two steps with approximately an equimolar amount of chlorine, the first step at about 0° to 80° C with all the reactants supplied, and the second step at about 0° to 100° C with precipitation of sulfur from the disulfur dichloride which is produced as a by-product in the first step and which serves as the chlorinating agent in the second step. Advantageously the first step is carried out continuously in two stages about one-third to two-thirds of the chlorine being supplied continuously to each stage. The first stage is at about 30° to 60° C and the second stage at about 10° to 25° C. The second step is thereafter performed batchwise and the desired product is distilled off from the residual sulfur.

5 Claims, No Drawings

PRODUCTION OF O,O-DIALKYL-PHOSPHOROCHLORIDOTHIONATES

The invention relates to a technically new and progressive process for the preparation of O,O-dialkyl-phosphorochloridothionates.

For the preparation of the above mentioned compounds the following different methods have been described in the chemical literature:

In U.S. Pat. No. 2,692,893 the preparation of O,O-dialkyl-phosphorochloridothionates is effected by reaction of the corresponding O,O-dialkyl-thionothiolphosphoric acids with elementary chlorine according to the following equation:

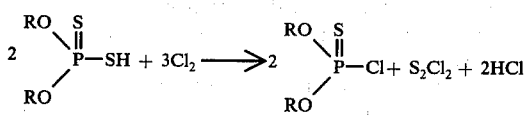

wherein R is an alkyl radical with 1 to 6 carbon atoms or a cycloalkyl radical with 5 or 6 carbon atoms.

Furthermore the reaction of di-(O,O-dialkyl-thionophosphoryl) disulfides with chlorine or disulfur dichloride is known from U.S. Pat. No. 2,482,063 according to the following chemical equations:

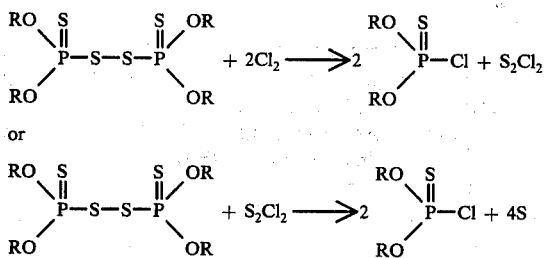

The O,O-dialkyl-phosphorochloridothionates can also be obtained.

These processes describing the present state of the art have several important disadvantages especially when used for large scale production.

The by-product disulfur dichloride that is formed during the chlorination is very difficult to separate from the reaction mixture. Depending on the process that is used for the separation, large amounts of heavily loaded waste waters are generated or considerable technical expenditure is required. An additional disadvantage of the known processes, where the chlorination is carried out with elementary chlorine up to the end point, is the necessity of adding the chlorination agent with great accuracy. In case not enough chlorine has been added, the reaction mixture contains di-(O,O-dialkyl-thiophosphoryl) disulfide. With an excess of chlorine, the generated O,O-dialkyl-phosphorochloridothionates continue to react, with formation of undesired side-products, e.g. alkylphosphorodichloridothionate of the structural formula

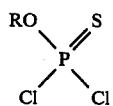

The yield of O,O-dialkyl-phosphorochloridothionates prepared according to this process is therefore in the case of the O,O-dimethyl-compound only 58% of theory based on O,O-dimethylthionothiolphosphoric acid charged. Furthermore the chlorination of O,O-dialkyl-thionothiolphosphoric acids or disulfides with commercially available disulfur dichloride as a technical process is not economically feasible. In addition, the amount of sulfur that has to be removed is considerably increased.

The present invention is characterized by performing the chlorination of the O,O-dialkyl-thionothiolphosphoric acid in two steps, whereby in the first step equimolar amounts of O,O-dialkyl phosphorodithionic acid and elementary chlorine are reacted and the by-product di-(O,O-dialkyl-thionophosphoryl) disulfide and the disulfur dichloride are reacted in the second reaction step.

The course of the inventive process can be explained based upon the following scheme of equations:

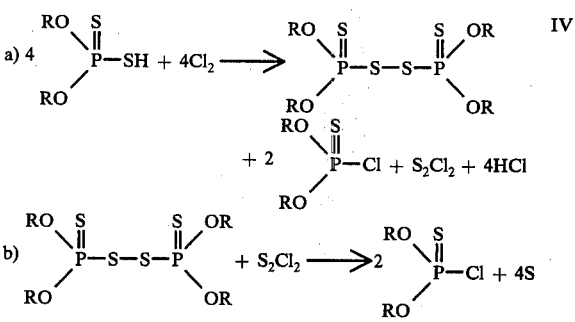

As is explained by these equations, in which R has the aforementioned meaning and is preferably alkyl of 1 to 6 carbon atoms or is cyclohexyl, in the first step 1 mole of di-(O,O-dialkyl-thiono-phosphoryl) disulfide, 1 mole of disulfur dichloride and 4 moles of HCl are formed in addition to 2 moles of O,O-dialkyl-phosphorochloridothionate. In the second step the disulfur dichloride formed as a by-product acts as a mild chlorinating agent on the simultaneously formed disulfide.

The smooth and clear course of the inventive process, according to which the claimed O,O-dialkyl-thionophosphoric ester chlorides can be obtained in excellent yields and high purity even under usage of only technical grade starting materials is completely surprising and could not be foreseen.

In case one uses, for example, for the chlorination in the first reaction step, technical O,O-dimethyl-thionothiolphosphoric acid with an acidimetrically determined content of 91%, there is obtained according to the present reaction a theoretical yield of 91.7% based upon the charged dithiophosphoric acid. Because the 9% byproducts (inherent) of the technical dithio acid still contains compounds that are also transformed into ester chlorides, for comparison of yields it is better to base the yield calculation on the amount of $P_2S_5$ used for the preparation of the corresponding acid. Based upon $P_2S_5$, the yield for the preparation of O,O-dimethyl-thionophosphoric acid ester chloride according to the present process is 83.7% of theory and is therefore much higher than for all other known processes.

The advantages of the invention, compared to the present state of the art, is quite obvious. The cumbersome and technically very expensive removal of the disulfur dichloride is no longer required; to the contrary, this by-product is used in the second reaction step for the final chlorination. Furthermore the chlorinated crude reaction product can be separated from the precipitated sulfur and by-products by a simple distillation at reduced pressure.

A further advantage of the claimed process is that the chlorination in the final step is carried out with the mild chlorinating agent disulfur dichloride. Since the disulfur dichloride generated in the first step is used for this purpose, approximately 30% of the amount of the chlorine normally required in other known processes is saved. A much larger advantage lies in the fact that the disulfur dichloride, even when used in excess, does not react easily with the generated O,O-dialkyl-thionophosphoric acid ester chloride with formation of the aforementioned by-products. Charging of the chlorine is much less complicated, which is most important with regard to the fact that the chlorine quantity has to be accurately adjusted to the crude O,O-dialkyl-dithiophosphoric acids having normally variations in quality (A.I.).

As already briefly stated above, the O,O-dialkylthionophosphoric acid ester chloride, which can be prepared according to the invention from technical O,O-dialkyl-dithiophosphoric acids in larger yield and which can be separated from the sulfur generated during the reaction by simple distillation at reduced pressure, is of such a high purity, that a fractional distillation is no longer required. If necessary, a subsequent washing with dilute caustic is indicated to remove remaining traces of impurities.

Inert solvents or diluents may be present during the reaction but do not provide any advantage. The reaction temperature can be varied over a large range and it is possible to perform the chlorination in the first step at from about 0° to 80° C. For continuous operation of the process it is specifically advantageous to operate below 30° C, preferably at 20° C, because at that temperature no sulfur precipitates.

In accordance with a preferred aspect of the invention, the first step can be effected continuously in two stages with the second step effected batchwise as described. In the continuous first step, two reactors are provided with product from the first stage continuously overflowing to the second and product from the second continuously overflowing to a holding vessel which is periodically emptied into a third reactor for effecting the second step. The starting acid is continuously supplied to the first reactor and about one third to two thirds of the total chlorine supplied is supplied to each of the first and second reactors. The temperature in the first reactor is kept at about 30° to 60° C, preferably about 40° to 50° C. The temperature in the second reactor is kept at about 10° to 25° C, preferably about 15° to 20° C. The material in both reactors is a solution with no evidence of any precipitated sulfur.

The temperature for the chlorination with the by-product disulfur dichloride is between about 0° and 100° C; it is of specific advantage to operate this second step of the reaction at about 40° to 90° C because the reaction rate at lower temperatures is too slow, whereas at higher temperatures increased decomposition of the desired material takes place. Under these conditions the reaction time for the second step of the chlorination is from about 1 to 24 hours, the exact value depending on the starting materials and the selected temperature.

For the reaction of O,O-dimethyl-dithiophosphoric acid according to the invention the reaction time amounts to about 1 to 5 hours at the specified temperatures. As already mentioned above and as is evident from equations IV (a) and (b), 1 mole of chlorine is theoretically required per mole of dithio acid. Generally, in practice about 0.9 to 1.1 moles per mole of crude dithio acid are used, the chlorine being introduced with agitation into the reaction mixture containing the charged dithio acid at the specified temperature.

After completion of the chlorine addition it is not necessary to isolate the intermediate reactants; on the contrary, the chlorination with the simultaneously generated disulfur dichloride is performed in a simple manner by agitation within the above-mentioned temperature range.

Finally the isolation and purification of the desired end product is achieved by distillation from the precipitated sulfur at reduced pressure.

The O,O-dialkyl-phosphorochloridothionates that are prepared according to the novel process are valuable intermediates for the production of pesticides based upon phosphoric acid esters.

The process is illustrated in the following examples wherein all parts are by weight unless otherwise expressed:

EXAMPLE 1

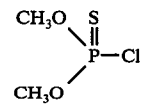

Into a four neck reaction flask equipped with agitator, reflux condenser, gas dip-tube and thermometer, there are charged 316 g (2 moles) of technical grade O,O-dimethyl-dithiophosphoric acid (91%) (according to acidimetric determination) and with intensive agitation 142 g (2) moles) of chlorine at 20° C over a period of 2 hours. The reaction mixture, from which no sulfur has precipitated, is postreacted for 5 hours at 50° C and then separated from the resulting sulfur precipitate by distillation. The product boils at 40°–42° C at 4 mm Hg.

The following yields were obtained:

| Distillate | 267.0 g |
|---|---|
| Residue | 91.0 g |
| Crude yield | 92% of theory |

(Crude yield based on consumption of $P_2S_5$: 83.7% of theory)

The O,O-dimethyl-phosphorochloridothionate has the following composition based upon gas chromatographic analysis:

| Unknown | 0.3% |
|---|---|
| O-methyl-thionophosphoric acid ester dichloride | 0.1% |
| O,O-dimethyl-phosphorochloridothionate | 99.6% |

EXAMPLE 2

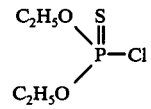

Into a four neck flask equipped with agitator, reflux condenser, inlet tube for gas, and thermometer and charged with 372 g (2 moles) of technical O,O-diethyl-thionothiolphosphoric acid with an acid content of 94.2%, 142 g (2 moles) of chlorine are injected under heavy agitation.

After the completion of the chlorine introduction no sulfur has been precipitated from the reaction mixture. The reaction solution is then stirred for 2 hours at 70° C; during this time sulfur precipitates; finally the reaction product is separated from the sulfur by distillation under reduced pressure; the product boils at 61°-63° C at 6 mm Hg.

The following yields are obtained:

| Distillate | 324 g |
|---|---|
| Residue | 103 g |
| Crude yield | 91.3% of theory |

(Crude yield based upon used $P_2S_5$: 86% of theory)

The product has the following composition according to gas chromatographic analysis:

| Unknown substances | 1.1% | |
|---|---|---|
| O-ethyl-thiono-phosphoric acid ester dichloride | 0.1% | $C_2H_5O-\underset{Cl}{\underset{|}{P}}-Cl$ with S double bond |
| O,O-diethyl-thionophosphoric acid ester chloride | 99.7% | $(C_2H_5O)_2 P-Cl$ with S double bond |
| O,O,O-triethyl-thionophosphoric acid ester | 0.1% | $(C_2H_5O)_3P=S$ |

EXAMPLE 3

Preparation of O,O-dimethyl-phosphorochloridothionate 632 g (4.0 moles) of crude dimethyldithiophosphoric acid prepared according to Malatesta et al, Gazz. Chim. Ital. 81 (1951) 596–608 (acidimetric content: 88%) are treated in a long flask provided with reflux condenser and gas outlet, thermometer and gas stirrer, as temperatures between 15° C and 25° C with 284 g (4.0 moles) of chlorine. The reaction is exothermic and requires ice water cooling. A strong hydrogen chloride stream escapes during the first half of the chlorination; during the second half of the reaction the liquid turns dark yellow. The introduction of chlorine is completed in 75–90 minutes with the cooling noted above.

The clear solution is heated for one hour at 90° C. Sulfur separates and the dark-yellow color becomes lighter. Subsequently, the O,O-dimethyl-phosphorochloridothionate is distilled off under vacuum ($Kp_4$ 40° C) or 40° C at 4 mm Hg from the sulfur-containing residue to a maximum sump temperature of 100° C. The crude distillate has a clear to light-yellowish color and hardly contains any sulfur chloride.

For further purification, the crude distillate is washed for 30 minutes at 20° C with dilute soda lye at pH 10.

The washed O,O-dimethyl-phosphorochloridothionate is separated from the alkaline water and traces of water are removed by vacuum distillation.

| Sulfur residue | about 187.0 g | |
|---|---|---|
| O,O-dimethyl-phosphoro-chloridothionate | 554.0 g = | 86.3% based on crude O,O-dimethyl-dithio-phosphoric acid |

| Content GC | 99.3% |
|---|---|
| Monoester | 0.1% |
| Triester | 0.1% |
| Unknowns | 0.3% |
| Water | 0.2% |

EXAMPLE 4

Preparation of O,O-diethyl-phosphorochloridothionate

In analogous manner, from 744.8 g (4.0 moles) of crude O,O-diethyl-dithiophosphoric acid (acidimetric content: 91%) and 284 g (4.0 moles) of chlorine there are obtained 671.0 g of O,O-diethyl-phosphorochloridothionate = 89.0% (based on crude acid) with a net

| content (GC) of: | 99.0% |
|---|---|
| Triester | 0.6% |
| Monoester | 0.2% |
| Water | 0.1% |
| Unknowns | 0.1% |

EXAMPLE 5

Partially-continuous process for the preparation of O,O-diethyl-phosphorochloridothionate Into a two-stage flask cascade with overflow in which two 1-liter reactors are both provided with a reflux condenser and gas outlet, a thermometer and a gas stirrer, up to the overflow in each flask there are placed 744.8 g (4.0 moles) of crude diethyl-dithiophosphoric acid for the start of the cascade. Independently of each other one passes into the first flask of the cascade 142 g (2.0 moles) of chlorine at 40°–50° C and into the second flask 284 g (4.0 moles) of chlorine at 15°–20° C.

Then additional crude diethyl-dithiophosphoric acid (372 g = 2.0 moles/hour) is dropped into flask 1 along with introduction of half the corresponding amount of chlorine (71 g = 1 mole/hour) at 40°–50° C. Chlorination of the overflowing semichlorinated reaction mixture is then finished in flask 2 at 15°–20° C with the second half of the required chlorine amount (71 g = 1 mole/hour). The discharged yellowish-brown clear solution is further reacted with separation of sulfur as described in Example 1.

The interruption of the continuous procedure is simple. The content of the second flask is ready for the additional processing, while the content of the first flask must still be treated for the completion of the reaction with the second half of chlorine.

It will be appreciated that the instant specification and examples are set forth by way of illustration and not limitation, and that various modifications and changes may be made without departing from the spirit and scope of the present invention.

What is claimed is:

1. In the reaction of O,O-dialkyl-dithiophosphoric acid ester with chlorine to produce an O,O-dialkyl-phosphorochloridothionate, the improvement which comprises effecting the chlorination in two steps, in the first step O,O-dialkyl-dithiophosphoric acid and about one-third to two-thirds of the chlorine being continuously reacted in a first stage at a temperature of about 30° to 60° C, material from the first stage along with the balance of the chlorine being continuously supplied to a second stage of the first step maintained at a temperature of about 10° to 25° C, with formation of a clear solution containing the desired product plus by-product di-(O,O-dialkyl-thionophosphoryl) disulfide and disulfurdichloride, the by-products formed in the first step reacting with each other in the second step at about 0° to 100° C with precipitation of sulfur and formation of further quantities of the desired product.

2. A process according to claim 1 wherein about 0.9 to 1.1 moles of chlorine are supplied per mole of O,O-dialkyl-dithiophosphoric acid.

3. A process according to claim 1, wherein the second reaction step is carried out between 40° and 95° C.

4. A process according to claim 1, wherein the reaction product is separated from the simultaneously formed sulfur and other non-volatile by-products by distillation under reduced pressure.

5. A process according to claim 2, wherein the first step is effected in the substantial absence of a solvent, the first stage is maintained at a temperature of about 40° to 50° C, and the second stage is maintained at a temperature of about 15° to 20° C.

* * * * *